US009562000B2

(12) United States Patent
Keil et al.

(10) Patent No.: US 9,562,000 B2
(45) Date of Patent: Feb. 7, 2017

(54) AMINO ALCOHOL TREATMENT FOR SOL-GEL CONVERSION COATINGS, SUBSTRATES INCLUDING THE SAME, AND METHODS OF MAKING THE SUBSTRATES

(71) Applicant: PRC-DeSoto International, Inc., Sylmar, CA (US)

(72) Inventors: Charles Keil, Mission Viejo, CA (US); Richard Albers, Irvine, CA (US)

(73) Assignee: PRC-DeSoto International, Inc., Sylmar, CA (US)

( * ) Notice: Subject to any disclaimer, the term of this patent is extended or adjusted under 35 U.S.C. 154(b) by 0 days.

(21) Appl. No.: 14/180,918

(22) Filed: Feb. 14, 2014

(65) Prior Publication Data

US 2015/0232413 A1   Aug. 20, 2015

(51) Int. Cl.
| | | |
|---|---|---|
| *C07C 215/10* | (2006.01) | |
| *C09D 175/04* | (2006.01) | |
| *B05D 1/00* | (2006.01) | |
| *C23C 18/12* | (2006.01) | |
| *C23C 28/00* | (2006.01) | |

(52) U.S. Cl.
CPC .............. *C07C 215/10* (2013.01); *B05D 1/00* (2013.01); *C09D 175/04* (2013.01); *C23C 18/1254* (2013.01); *C23C 18/1295* (2013.01); *C23C 28/00* (2013.01); *B05D 2503/00* (2013.01); *Y10T 428/31551* (2015.04)

(58) Field of Classification Search
CPC .. C23C 18/1254; C23C 18/1295; C23C 28/00; C07C 215/10; C09D 175/04; Y10T 428/31551; Y10T 428/31605; Y10T 428/31609; B05D 1/00; B05D 2503/00
USPC ............................................ 428/411.1, 423.1
See application file for complete search history.

(56) References Cited

U.S. PATENT DOCUMENTS

| | | | |
|---|---|---|---|
| 2,967,771 A * | 1/1961 | Kaner et al. .................. 430/463 |
| 4,417,998 A * | 11/1983 | Kennedy ................. 252/182.27 |
| 5,789,085 A | 8/1998 | Blohowiak et al. |
| 5,814,137 A | 9/1998 | Blohowiak et al. |
| 5,849,110 A | 12/1998 | Blohowiak et al. |
| 5,866,652 A | 2/1999 | Hager et al. |
| 5,869,140 A | 2/1999 | Blohowiak et al. |
| 5,869,141 A | 2/1999 | Blohowiak et al. |
| 5,939,197 A | 8/1999 | Blohowiak et al. |
| 6,733,837 B1 | 5/2004 | Dees |
| 7,422,793 B2 | 9/2008 | Phelps et al. |
| 2004/0194663 A1* | 10/2004 | Li et al. ........................ 106/403 |
| 2006/0134160 A1* | 6/2006 | Troczynski ............. A61L 27/32 424/422 |
| 2006/0204767 A1 | 9/2006 | Albert et al. |
| 2008/0233315 A1* | 9/2008 | Aoshima et al. ............ 428/32.1 |

(Continued)

*Primary Examiner* — Thao T Tran
(74) *Attorney, Agent, or Firm* — Alicia M. Passerin

(57) ABSTRACT

An article includes a substrate, a sol-gel conversion coating on at least a portion of the substrate, and a treatment layer on at least a portion of the sol-gel conversion coating. The treatment layer includes an amino alcohol. A method of manufacturing the article includes applying a partially cured sol-gel composition to at least a portion of a substrate, at least partially drying the partially cured sol-gel composition to form the sol-gel conversion coating, applying a solution including an amino alcohol to at least a portion of the sol-gel conversion coating, and at least partially drying the solution including the amino alcohol.

12 Claims, 4 Drawing Sheets

(56) References Cited

U.S. PATENT DOCUMENTS

| | | |
|---|---|---|
| 2009/0244709 A1 | 10/2009 | Suzuki et al. |
| 2012/0308830 A1* | 12/2012 | Wayton .................... C09D 5/08 428/413 |
| 2013/0022839 A1 | 1/2013 | Kijima et al. |
| 2014/0037841 A1 | 2/2014 | Jawhurst et al. |

* cited by examiner

AMINO ALCOHOL TREATMENT FOR SOL-GEL CONVERSION COATINGS, SUBSTRATES INCLUDING THE SAME, AND METHODS OF MAKING THE SUBSTRATES

TECHNICAL FIELD

Embodiments of the present disclosure are directed toward an article including a substrate, a sol-gel conversion coating on the substrate, and a treatment layer on the sol-gel conversion coating, the treatment layer including an amino alcohol.

BACKGROUND

Coatings, such as conversion coatings, can be used to protect substrates, such as metal and/or metal alloy substrates. Conversion coatings can protect the substrate from corrosion and can be used as a primer for other coatings, such as topcoats and paints. For example, the conversion coating can attach (e.g., adhere) another coating to the substrate. Thus, a conversion coating should exhibit good adhesion to the substrate and to the other coating, if present. A conversion coating formed by way of a sol-gel process is referred to herein as a "sol-gel conversion coating."

SUMMARY

An embodiment of an article includes: a substrate; a sol-gel conversion coating on at least a portion of the substrate; and a treatment layer on at least a portion of the sol-gel conversion coating, the treatment layer including an amino alcohol.

Another embodiment of an article includes: a substrate; a sol-gel conversion coating on at least a portion of the substrate; a treatment layer on at least a portion of the sol-gel conversion coating, the treatment layer including an amino alcohol; and a coating layer on at least a portion of the treatment layer, the coating layer including a polyurethane-based coating composition.

BRIEF DESCRIPTION OF THE DRAWINGS

The accompanying drawings, together with the specification, illustrate embodiments of the present disclosure, and, together with the description, serve to explain principles of the present disclosure.

DETAILED DESCRIPTION

Figure 1:
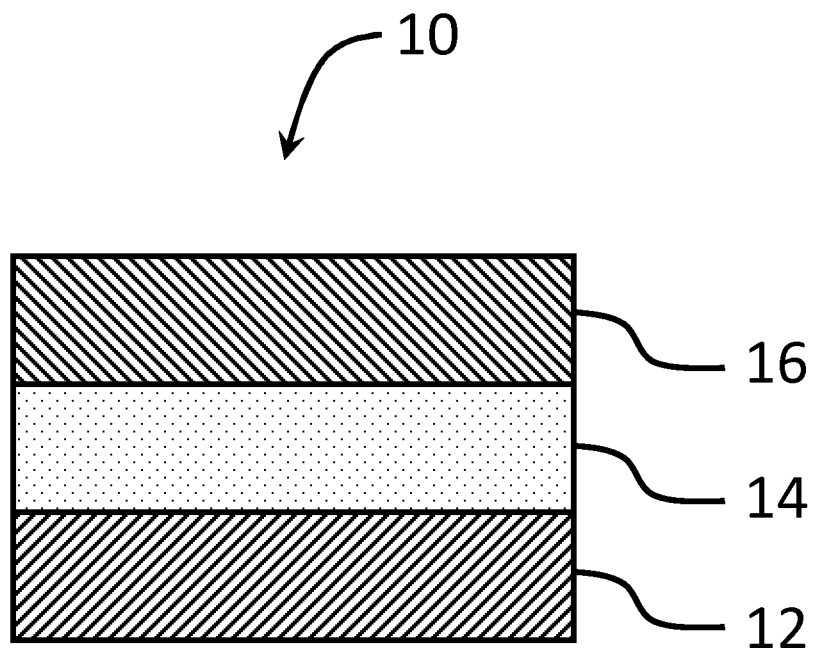
FIG. 1 is a schematic cross-sectional view of an article according to an embodiment of the present disclosure.

In the following detailed description, only certain embodiments are shown and described, by way of illustration. As those skilled in the art would recognize, the invention may be embodied in many different forms and should not be construed as being limited to the embodiments set forth herein. Also, in the context of the present application, when a first element is referred to as being "on" a second element, it can be directly on the second element or be indirectly on the second element with one or more intervening elements interposed therebetween. Like reference numerals designate like elements throughout the specification.

Embodiments of the present disclosure are directed toward an article including a treatment layer including an amino alcohol. In certain embodiments, the article includes a coated substrate. For example, in the embodiment illustrated in FIG. 1, an article 10 includes a substrate 12, a sol-gel conversion coating 14 on the substrate 12 (e.g., on at least a portion of the substrate 12), and the treatment layer 16 on the sol-gel conversion coating 14 (e.g., on at least a portion of the sol-gel conversion coating 14).

The treatment layer including the amino alcohol can improve adhesion of a coating layer to the sol-gel conversion coating, thereby improving adhesion of the coating layer to the substrate. In certain embodiments, the amino alcohol reacts with a functional group of the sol-gel conversion coating, which may be partially or fully cured, and separately (or concurrently) reacts with a functional group of the coating layer to attach (or adhere) the coating layer to the substrate. For example, a sol-gel conversion coating can have a surface including epoxy groups that can react with an amine group of the amino alcohol disclosed herein. In certain embodiments, an amine group of the presently described amino alcohol reacts with an epoxy group of the sol-gel conversion coating to form an amine linkage. The amine linkage of the amino alcohol and the sol-gel conversion coating can attach (e.g., adhere) the treatment layer to the sol-gel conversion coating.

Figure 2:
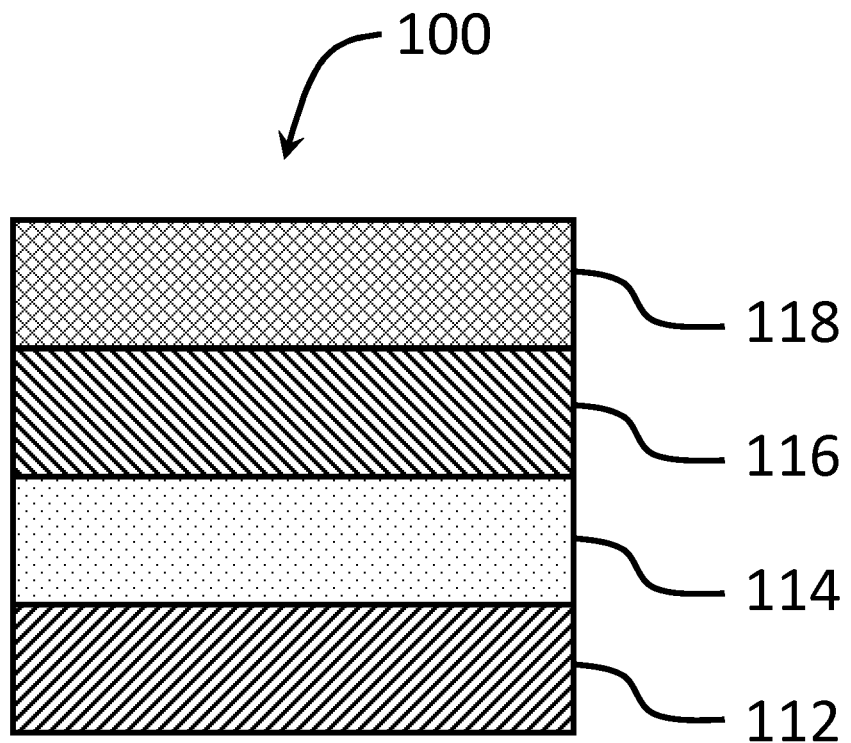
FIG. 2 is a schematic cross-sectional view of an article according to another embodiment of the present disclosure.

The amino alcohol of the treatment layer further includes a hydroxyl group that can react with certain functional groups of other layers, compositions or compounds. For example, a hydroxyl group of the amino alcohol can react with an isocyanate group of a coating composition to form a urethane linkage. The urethane linkage of the amino alcohol and the isocyanate can attach (e.g., adhere) a coating layer formed from the coating composition to the treatment layer, thereby attaching the coating to the substrate. As such, in certain embodiments, the treatment layer functions as a tie coat (e.g., a tie layer). For example, in the embodiment illustrated in FIG. 2, an article 100 includes a coated substrate including a substrate 112, a sol-gel conversion coating 114 on the substrate 112 (e.g., on at least a portion of the substrate 112), a treatment layer 116 on the sol-gel conversion coating 114 (e.g., on at least a portion of the sol-gel conversion coating 114), and a coating layer 118 on the treatment layer 116 (e.g., on at least a portion of the treatment layer 116).

In certain embodiments, the coating layer includes or is formed from a polyurethane-based coating composition. For example, the coating layer can be formed from a coating composition including hydroxyl functional polyols and polyisocyanates, and the coating layer can include a polyurethane. The polyurethane can be attached to (e.g., adhered to) the treatment layer via the urethane linkage formed with the amino alcohol. Coating compositions including hydroxyl functional polyols and polyisocyanates, and coating layers formed therefrom, such as a coating layer including a polyurethane, generally do not include functional groups that are readily reactive with the epoxy groups of the sol-gel conversion coating. As such, coating layers that include polyurethanes or coating layers formed from coating compositions including hydroxyl functional polyols and isocyanates do not adhere well to the sol-gel conversion coating. By including the amino alcohol in the treatment layer, embodiments of the present disclosure improve adhesion of the sol-gel conversion coating to a coating composition and/or a coating layer formed from the coating composition.

As used herein, the term "amino alcohol" refers to a compound including an amine group (e.g., one or more amine groups) and a hydroxyl group (e.g., one or more hydroxyl groups). In the context of the present disclosure, the amine group and/or hydroxyl group of the amino alcohol can be reacted or unreacted. For example, when the treatment layer is referred to as including an amino alcohol, the amino alcohol can include an unreacted amine group and/or an amine group that has reacted with a functional group, such as an epoxy group, of another compound, but the present disclosure is not limited thereto. The amino alcohol can also include an unreacted hydroxyl group and/or a hydroxyl group that has reacted with a functional group, such as an isocyanate group, of still another compound, but the present disclosure is not limited thereto.

The amino alcohol can include any suitable compound that includes an amine group (e.g., one or more amine groups) and a hydroxyl group (e.g., one or more hydroxyl groups). For example, the amino alcohol can include any suitable oligomer and/or polymer that includes an amine group and a hydroxyl group, or any suitable mixture of such oligomers and/or polymers. The amino alcohol can include a compound that is a room temperature solid or liquid. In certain embodiments, when the amino alcohol is a room temperature liquid, a coating layer on the treatment layer exhibits better wet adhesion to the treatment layer (or substrate) than does a coating layer on a treatment layer including an amino alcohol that is a room temperature solid. While the present disclosure is not limited by any particular mechanism or theory, it is believed that an amino alcohol that is a room temperature liquid may provide better adhesion than that provided by an amino alcohol that is a room temperature solid as a result of improved mobility of the liquid amino alcohol on the surface of the sol-gel conversion coating, thereby increasing an amount of reaction of the liquid amino alcohol with functional groups (e.g., epoxy groups) of the sol-gel conversion coating. Nonetheless, the amino alcohol can include a room temperature solid.

The amino alcohol can include any suitable number of hydroxyl groups. An amino alcohol including a higher number of hydroxyl groups, however, will result in a coating layer that has a greater water sensitivity than that of a coating layer on a treatment layer including an amino alcohol including a relatively lower number of hydroxyl groups. Thus, in certain embodiments, the amino alcohol includes 1 to 3 hydroxyl groups, and, in certain embodiments, the amino alcohol includes a sole hydroxyl group, but the amino alcohol is not limited thereto.

The amino alcohol can include any suitable number of amine groups. In certain embodiments, the amino alcohol includes 1 to 3 amine groups, and, in certain embodiments, the amino alcohol includes a sole amine group, but the amino alcohol is not limited thereto.

The amino alcohol can include a compound represented by $[N(R_1)(R_2)]_z$—R—$(R'$—$OH)_x R''_y$, but the amino alcohol is not limited thereto. As set forth above, the amino alcohol can include any suitable number of amine groups and any suitable number of hydroxyl groups. For example, z can be 1 to 3, and x can be 1 to 3. In the amine group, $R_1$ and $R_2$ can each independently be any suitable functional group. For example, $R_1$ and $R_2$ can each independently be a hydrogen atom or a C1 to C6 alkyl group. When z is greater than 1, each $R_1$ and each $R_2$ may be the same or different. As the steric size of $R_1$ and/or $R_2$ increases, however, the reactivity of the amine group of the amino alcohol decreases. For example, an amino alcohol including the above-described compound in which $R_1$ and $R_2$ are each a hydrogen atom has an amine group having higher reactivity than that of a compound in which $R_1$ and $R_2$ are each a t-butyl group. Thus, the reactivity of the amine group of the amino alcohol may be controlled by controlling the steric size of $R_1$ and $R_2$. In certain embodiments, $R_1$ and $R_2$ are each a hydrogen atom.

In the compound represented by $[N(R_1)(R_2)]_z$—R—$(R'$—$OH)_x R''_y$, R, R' and R'' can be any suitable hydrocarbon-based linking group. As used herein, the term "hydrocarbon-based linking group" refers to a linking group including hydrogen and carbon as the main atoms of the compound, and includes cyclic, aromatic and aliphatic linking groups, as would be understood by those of ordinary skill in the art. For example, in some embodiments, R and R' can each independently include a C1 to C30 alkylene group, and R'' can include a hydrogen atom or a C1 to C30 alkyl group. When x is greater than 1, each of R's can be the same or different, and when y is greater than 1, each of the R''s can be the same or different. In certain embodiments, y can be 0 to 2, and x+y+z=4.

Examples of the amino alcohol include tris(hydroxymethyl)aminomethane, amino methyl propanediol, amino ethyl propanediol, amino methyl propanol, dimethyl amino ethanol, amino hydroxyethyl pentanediol, amino pentanediol, and amino methyl butanol, but the amino alcohol is not limited thereto. For example, some additional non-limiting examples of suitable amino alcohols include, 2-amino ethanol (i.e., monoethanolamine), 2,2' iminodiethanol (i.e., diethanolamine), tris(2-hydroxyethyl) amine (i.e., triethanolamine), N-hydroxyethyl ethylene diamine, N-hydroxyethyl pentamethylene diamine, N-hydroxypropyl tetramethylene diamine, N-hydroxyethyl diethylene triamine, N,N-dihydroxyethyl diethylene triamine, N,N''-dihydroxyethyl diethylene triamine, N-hydroxypropyl diethylene triamine, N,N-dihydroxypropyl diethylene triamine, N,N''-dihydroxypropyl diethylene triamine, N-hydroxyethyl propylene diamine, N-hydroxypropyl propylene diamine, N-hydroxyethyl dipropylene triamine, N-dihydroxyethyl dipropylene triamine, N,N'-dihydroxyethyl dipropylene triamine, and tris-hydroxyethyl triethylene tetramine. In certain embodiments, the amino alcohol includes tris(hydroxymethyl)aminomethane. In certain embodiments, the amino alcohol includes dimethyl amino ethanol and/or amino hydroxyethyl pentanediol.

The sol-gel conversion coating can include any suitable sol-gel conversion coating used in the art. For example, the sol-gel conversion coating can include a sol-gel film as described in U.S. Pat. Nos. 5,789,085; 5,814,137; 5,849,110; 5,869,140; 5,869,141; and 5,939,197, but the sol-gel conversion coating is not limited thereto. Examples of the sol-gel conversion coating include those formed from a sol-gel composition including an effective amount (e.g., an amount up to 1 vol % of the sol-gel composition) of an organometallic including an alkoxyzirconium, yttrium acetate trihydrate, yttrium 2-ethylhexanoate, i-proproxyttrium, methoxyethoxyttrium, yttrium nitrate, cerium acetate hydrate, cerium acetylacetonate hydrate, cerium 2-ethylhexanolate, i-propoxycerium, cerium stearate, cerium nitrate, lanthanum nitrate hexahydrate, lanthanum acetate hydrate, lanthanum acetylacetonate, or a mixture thereof; and an effective amount of a reactive organosilane for complexing with the organometallic, but the sol-gel composition is not limited thereto. For example, the sol-gel conversion coating can be formed from a sol-gel composition including a zirconium and an organosilane (e.g., the sol-gel conversion coating can include an epoxy silane zirconate or an amino silane zirconate). A commercially available example of a sol-gel composition includes Desogel EAP-9 (available from PPG Aerospace). The sol-gel composition can further include an organic acid catalyst and a zirconium stabilizer. Those of ordinary skill in the art would readily understand how to prepare such a sol-gel conversion coating. For example, those of ordinary skill in the art would readily understand that the performance of the sol-gel composition can be controlled by controlling the Si/Zr ratio, the ratio of components in the sol-gel composition, the concentration of the sol-gel composition, the carrier solvent, solution age, catalysts, surface pretreatment, application method and curing process. Thus, the preparation and composition of the sol-gel conversion coating will not be further described here.

The coating layer can include any suitable polyurethane, but the coating layer is not limited thereto. For example, the coating layer can be formed from the reaction of hydroxyl functional polyols and organic polyisocyanates. Suitable polyurethane coatings include two-part coating compositions, but the coating layer is not limited thereto. The two-part composition can include a base component and an activator component. The activator component can include compounds having isocyanate functionality, and the base component can include compounds having hydroxyl functionality. The base and activator components can be mixed just prior to the application of the coating composition to form the coating layer. Upon being mixed and coated onto a substrate, the coating composition cures as the isocyanate groups in the activator component react with the hydroxyl groups in the base component, yielding the polyurethane coating. Some of the isocyanate groups in the activator component react with the hydroxyl groups of the amino alcohol to attach the coating layer to the sol-gel conversion layer. An example of a commercially available coating composition includes DEFTHANE® ELT (DEFTHANE® is a registered trademark of PRC-DeSoto International, Inc., Sylmar, Calif.), but the coating composition is not limited thereto. The coating composition can also include a corrosion inhibitor.

The coating composition may further include conventional additives for coating compositions, such as catalysts, colorants, fillers, UV absorbers, flow aids, and rheology control agents. Catalysts promote the curing reaction and may include tertiary amines, metal compound catalysts, or combinations thereof. Examples of suitable tertiary amine catalysts include triethylamine, N-methylmorpholine, triethylenediamine, pyridine, picoline, and the like, but the catalyst is not limited thereto. Examples of suitable metal compound catalysts include compounds of lead, zinc, cobalt, titanate, iron, copper, and tin, but the metal compound catalyst is not limited thereto. For example, the metal compound catalyst may be lead 2-ethylhexoate, zinc 2-ethylhexoate, cobalt naphthenate, tetraisopropyl titanate, iron naphthenate, copper naphthenate, dibutyl tin diacetate, dibutyl tin dioctate, dibutyl tin dilaurate, and the like.

When used, the catalyst can be present in a total amount of 0.001 to 0.05 weight percent based on the total weight of the resin solids in the coating composition. For example, the catalyst can be present in an amount of 0.005 to 0.02 weight percent based on the total weight of the resin solids in the coating composition.

Rheology modifiers refer to compounds that can modify the flow and leveling properties of the coating formulation. The coating formulation should have suitable flow and leveling characteristics such that it can be coated uniformly over the surface of the treatment layer. The coating composition can be adjusted in any way to suit the needs of the user, such as by adjusting rheology, viscosity, surface tension, level of functionality and the like. These adjustments can be made, for example, by adjusting the resin molecular weight, solvent composition, coating formulation solids, application process, coating film thickness, coating reactivity, pigment composition and concentration, and rheological flow additive composition and concentration.

As used herein, the term "colorant" means any substance that imparts color and/or other opacity and/or other visual effect to the coating composition (or coating layer). The colorant can be added to the coating composition (or coating layer) in any suitable form, such as discrete particles, dispersions, solutions and/or flakes. A single colorant or a mixture of two or more colorants can be used in the coatings of the present invention. A "filler," on the other hand, does not necessarily impart any color and/or opacity and/or other visual effect to the coating composition (or coating layer).

Example colorants include pigments, dyes and tints, such as those used in the paint industry and/or listed in the Dry Color Manufacturers Association (DCMA), as well as special effect compositions. A colorant may include, for example, a finely divided solid powder that is insoluble but wettable under the conditions of use. A colorant can be organic or inorganic and can be agglomerated or non-agglomerated. Colorants can be incorporated into the coating composition (or coating layer) by grinding or simple mixing. Colorants can be incorporated by grinding into the coating composition (or coating layer) by use of a grind vehicle, such as an acrylic grind vehicle, the use of which will be familiar to one skilled in the art.

Example pigments and/or pigment compositions include, but are not limited to, carbazole dioxazine crude pigment, azo, monoazo, disazo, naphthol AS, salt type (lakes), benzimidazolone, condensation, metal complex, isoindolinone, isoindoline and polycyclic phthalocyanine, quinacridone, perylene, perinone, diketopyrrolo pyrrole, thioindigo, anthraquinone, indanthrone, anthrapyrimidine, flavanthrone, pyranthrone, anthanthrone, dioxazine, triarylcarbonium, quinophthalone pigments, diketo pyrrolo pyrrole red ("DPPBO red"), titanium dioxide, carbon black, carbon fiber, graphite, other conductive pigments and/or fillers and mixtures thereof. The terms "pigment" and "colored filler" can be used herein interchangeably.

Example dyes include, but are not limited to, those that are solvent- and/or aqueous-based such as acid dyes, azoic dyes, basic dyes, direct dyes, disperse dyes, reactive dyes, solvent dyes, sulfur dyes, mordant dyes, for example, bismuth vanadate, anthraquinone, perylene aluminum, quinacridone, thiazole, thiazine, azo, indigoid, nitro, nitroso, oxazine, phthalocyanine, quinoline, stilbene, and triaryl methane.

Example tints include, but are not limited to, pigments dispersed in water-based or water-miscible carriers such as AQUA-CHEM 896 commercially available from Degussa, Inc., CHARISMA COLORANTS and MAXITONER INDUSTRIAL COLORANTS commercially available from Accurate Dispersions division of Eastman Chemicals, Inc.

As noted above, the colorant can be in the form of a dispersion including, but not limited to, a nanoparticle dispersion. Nanoparticle dispersions can include one or more highly dispersed nanoparticle colorants and/or colorant particles that produce a desired visible color and/or opacity and/or visual effect. Nanoparticle dispersions can include colorants such as pigments or dyes having a particle size of less than 150 nm, such as less than 70 nm, or less than 30 nm. Nanoparticles can be produced by milling stock organic or inorganic pigments with grinding media having a particle size of less than 0.5 mm. Example nanoparticle dispersions and methods for making them are identified in U.S. Pat. No. 6,875,800 B2, which is incorporated herein by reference. Nanoparticle dispersions can also be produced by crystallization, precipitation, gas phase condensation, and chemical attrition (i.e., partial dissolution).

In order to minimize re-agglomeration of nanoparticles within the coating composition (or coating layer), a dispersion of resin-coated nanoparticles can be used. As used herein, a "dispersion of resin-coated nanoparticles" refers to a continuous phase in which is dispersed discrete "composite microparticles" that comprise a nanoparticle and a resin coating on the nanoparticle. Example dispersions of resin-coated nanoparticles and methods for making them are described, for example, in U.S. Pat. No. 7,605,194 at col. 3, line 56 to col. 16, line 25, the cited portion of which being incorporated herein by reference. Coated particles, such as aluminum oxide coated with titanium dioxide, can also be used.

Example special effect compositions that may be used include pigments and/or compositions that produce one or more appearance effects such as reflectance, pearlescence, metallic sheen, phosphorescence, fluorescence, photochromism, photosensitivity, thermochromism, goniochromism and/or color-change. Additional special effect compositions can provide other perceptible properties, such as opacity or texture. In a non-limiting embodiment, special effect compositions can produce a color shift, such that the color of the coating changes when the coating is viewed at different angles. Example color effect compositions are identified in U.S. Pat. No. 6,894,086, incorporated herein by reference. Additional color effect compositions can include transparent coated mica and/or synthetic mica, coated silica, coated alumina, a transparent liquid crystal pigment, a liquid crystal coating, and/or any composition wherein interference results from a refractive index differential within the material and not because of the refractive index differential between the surface of the material and the air.

In certain non-limiting embodiments, a photosensitive composition and/or photochromic composition, which reversibly alters its color when exposed to one or more light sources, can be used in the coating composition (or coating layer) of the present invention. Photochromic and/or photosensitive compositions can be activated by exposure to radiation of a specified wavelength. When the composition becomes excited, the molecular structure is changed and the altered structure exhibits a new color that is different from the original color of the composition. When the exposure to radiation is removed, the photochromic and/or photosensitive composition can return to a state of rest, in which the original color of the composition returns. In one non-limiting embodiment, the photochromic and/or photosensitive composition can be colorless in a non-excited state and exhibit a color in an excited state. Full color-change can appear within milliseconds to several minutes, such as from 20 seconds to 60 seconds. Example photochromic and/or photosensitive compositions include photochromic dyes.

In a non-limiting embodiment, the photosensitive composition and/or photochromic composition can be associated with and/or at least partially bound to, such as by covalent bonding, a polymer and/or polymeric materials of a polymerizable component. In contrast to some coatings in which the photosensitive composition may migrate out of the coating composition (or coating layer) and crystallize into the substrate, the photosensitive composition and/or photochromic composition associated with and/or at least partially bound to a polymer and/or polymerizable component in accordance with a non-limiting embodiment of the present invention, have minimal migration out of the coating composition (or coating layer). Example photosensitive compositions and/or photochromic compositions and methods for making them are identified in U.S. Pat. No. 8,153,344 B2, and incorporated herein by reference.

In general, the colorant can be present in any amount sufficient to impart the desired visual and/or color effect. The colorant may comprise from 1 to 65 weight percent of the present coating compositions, such as from 3 to 40 weight percent or 5 to 35 weight percent, with weight percent based on the total weight of the coating compositions.

An "abrasion-resistant particle" is one that, when used in a coating composition (or coating layer), will impart some level of abrasion resistance to the coating layer as compared with the same coating layer lacking the particles. Suitable abrasion-resistant particles include organic and/or inorganic particles. Examples of suitable organic particles include, but are not limited to, diamond particles, such as diamond dust particles, and particles formed from carbide materials; examples of carbide particles include, but are not limited to, titanium carbide, silicon carbide and boron carbide. Examples of suitable inorganic particles, include but are not limited to silica; alumina; alumina silicate; silica alumina; alkali aluminosilicate; borosilicate glass; nitrides including boron nitride and silicon nitride; oxides including titanium dioxide and zinc oxide; quartz; nepheline syenite; zircon such as in the form of zirconium oxide; buddeluyite; and eudialyte. Particles of any size can be used, as can mixtures of different particles and/or different sized particles. For example, the particles can be microparticles, having an average particle size of 0.1 to 50, 0.1 to 20, 1 to 12, 1 to 10, or 3 to 6 microns, or any combination within any of these ranges. The particles can be nanoparticles, having an average particle size of less than 0.1 micron, such as 0.8 to 500, 10 to 100, or 100 to 500 nanometers, or any combination within these ranges.

The coating composition can be applied to at least a portion of the treatment layer using any suitable coating method, such as spray coating, gravure coating, die coating, dip coating, or printing, but the method is not limited thereto. The coating layer can have any suitable dry film thickness, such as 0.5 to 5 mils (e.g., 12 μm to 130 μm), but the coating layer is not limited thereto. The coating composition can be cured using any suitable technique, such as heat, UV, or NIR (near infrared radiation), but the curing is not limited thereto. Those of skill in the art will readily appreciate the conditions for curing the coating composition and, therefore, those conditions will not be further described here.

Although the present disclosure has been described with respect to the adhesion of a coating layer including a polyurethane or a coating layer formed from a composition including hydroxyl functional polyols and polyisocyanates to a sol-gel conversion coating layer, the present disclosure is not limited thereto, and the treatment layer and/or solution including an amino alcohol can be used to adhere any two layers together that have functional groups that are suitably reactive with the functional groups of the amino alcohol.

In certain embodiments, the substrate includes a metal and/or a metal alloy. For example, the substrate can include aluminum, aluminum alloys (e.g., zinc-aluminum alloys), titanium, titanium alloys, composite material (e.g., carbon-fiber reinforced polymer), steel (e.g., sheet steel, cold rolled steel, electrogalvanized steel, hot-dipped galvanized steel, aluminum plated steel, aluminum alloy plated steel, and/or stainless steel), cast iron, non-ferrous metals (e.g., brass, bronze, and/or magnesium, copper, silver, gold and/or alloys thereof), epoxy, urethane, graphite, acrylics, and/or polycarbonates and/or, but the substrate is not limited thereto. As used herein, the term "carbon-fiber reinforced polymer" refers to any suitable carbon-fiber reinforced plastic, carbon-fiber reinforced thermoplastic, or carbon fiber, and can include any suitable polymer (e.g., a thermoset or thermoplastic polymer or resin), such as epoxy, polyester, vinyl ester and/or nylon, and a reinforcing fiber, such as carbon fiber, aramid fiber, aluminum fiber and/or glass fiber.

Figure 3:
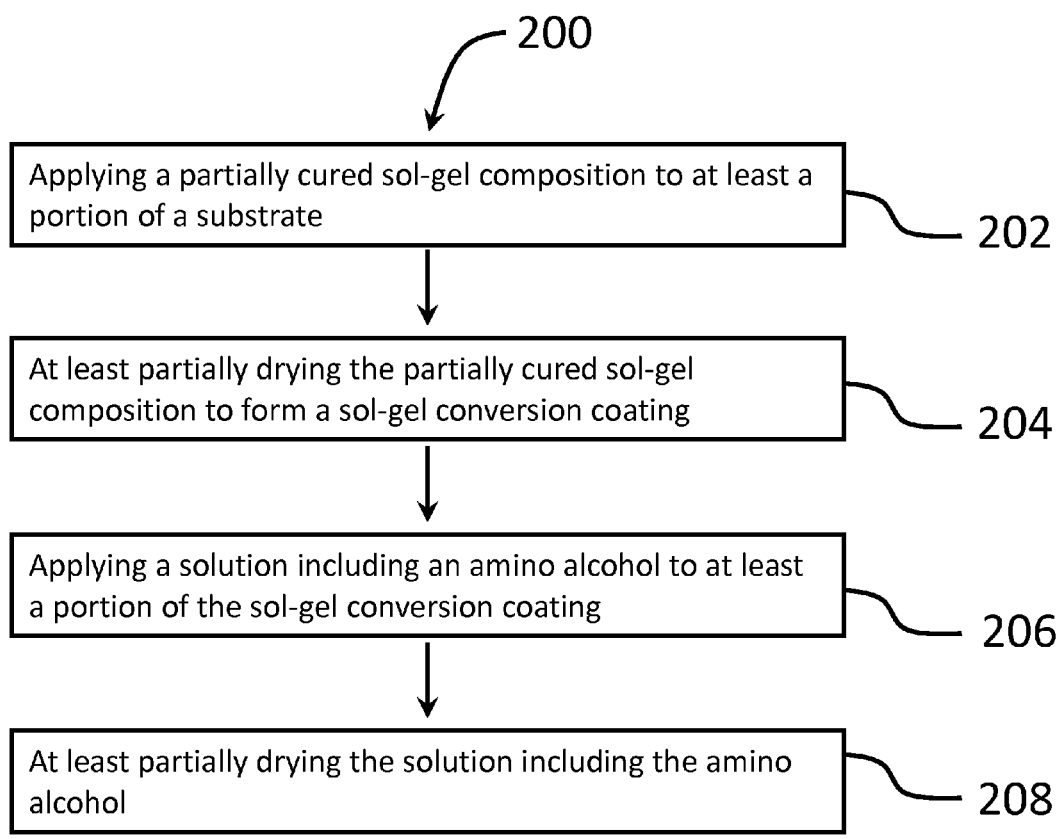
FIG. 3 is a flowchart illustrating a method of manufacturing an article according to an embodiment of the present disclosure.

A method of manufacturing an article according to an embodiment of the present disclosure is illustrated by the flowchart of FIG. 3. According to that embodiment, a method (200) includes applying a partially cured sol-gel composition to at least a portion of a substrate (202). For example, prior to being applied on the substrate, a sol-gel composition may be mixed and catalyzed (e.g., for a time period of 30 minutes) to form the partially cured sol-gel composition. The method (200), however, is not limited to applying a partially cured sol-gel composition to at least a portion of a substrate (202), but may instead include applying an uncured sol-gel composition to at least a portion of the substrate. The sol-gel composition and substrate can be any suitable sol-gel composition and substrate, such as those described above. The method further includes at least partially drying the sol-gel composition to form a sol-gel conversion coating (204) (e.g., a partially or fully cured sol-gel conversion coating). The method may also include further curing (e.g., further partially curing) the partially cured sol-gel composition to form the sol-gel conversion coating (e.g., the partially or fully cured sol-gel conversion coating). When the method includes applying an uncured sol-gel composition to at least a portion of the substrate, the method can include at least partially curing the uncured sol-gel composition.

According to embodiments of the present disclosure, the article can include, but is not limited to, a vehicle or a part or component of the vehicle. "Vehicle" is used herein in its broadest sense and includes all types of vehicles, such as but not limited to cars, trucks, buses, vans, heavy duty equipment, airplanes, golf carts, motorcycles, bicycles, railroad cars and the like. For example, the vehicle can include aerospace vehicles (e.g., airplanes), including, but not limited to, large commercial and freight airplanes, helicopters, rockets, and other spacecraft. As such, the article can include any number of vehicle parts or components, including, for example aerospace vehicle parts and components.

The at least partially drying and/or further curing of the partially cured sol-gel composition to form the sol-gel conversion coating may be carried out for a time period of 10 minutes to 20 hours, or, for example, 10 minutes to 16 hours, but the present disclosure is not limited thereto. In certain embodiments, the at least partially drying and/or further curing of the partially cured sol-gel composition to form the sol-gel conversion coating may be carried out for a time period of less than 24 hours. For example, when the sol-gel conversion coating includes an epoxy silane zirconate or an amino silane zirconate (e.g., the sol-gel conversion coating is formed from a sol-gel composition including a zirconium and an organosilane) and the at least partially drying and/or further curing of the partially cured sol-gel composition is carried out for a time period of more than 24 hours (or the sol-gel conversion coating is fully cured), the ability of the amino alcohol to wet the sol-gel conversion coating may be decreased and the ability of the amino alcohol to form the treatment layer may be impaired. The foregoing time periods are based on the at least partially drying and/or further curing being performed at standard temperature and pressure. As such, altering the temperature and/or pressure may affect the drying and/or curing time, which may also be affected by changes in other conditions, such as relative humidity. For example, when the temperature is increased above room temperature, the time period for at least partially drying and/or further curing the sol gel conversion coating may be decreased.

The method (200) further includes applying a solution including an amino alcohol to the sol-gel conversion coating (206) (e.g., on at least a portion of the partially or fully cured sol-gel conversion coating). The amino alcohol may be present in the solution at any concentration. For example, in certain embodiments, the treatment layer is formed from a solution consisting essentially of or consisting of the amino alcohol. In this context, "consisting essentially of" means that any additional components in the solution will not materially affect the adhesion of the treatment layer formed from the solution to another layer, such as the sol-gel conversion layer and/or coating layer.

In other embodiments, the solution further includes water (e.g., the solution is an aqueous solution) or an organic solvent. The organic solvent can be any suitable solvent capable of dissolving the amino alcohol. For example, the organic solvent can include an organic compound capable of dissolving the amino alcohol in an amount of 0.5 wt % or more, based on the total weight of the solution, but the organic solvent is not limited thereto.

The amino alcohol may be present in the solution in an amount of greater than 0 (for example, greater than 0.05 w/w %) to the solubility limit of the amino alcohol in the water or organic solvent. The solubility limit of the amino alcohol in water or the organic solvent can be readily determined by those of ordinary skill in the art. For example, to determine the solubility of an amino alcohol that is solid at room temperature, the solubility limit can be determined by dissolving an excess amount of the solid amino alcohol in the desired solvent, filtering the resultant to remove the undissolved amino alcohol from the solution, and then determining the solubility using gravimetric methodology. Amino alcohols that are less than 4 carbon atoms in length and that are liquid at room temperature are generally miscible in all proportions.

In some embodiments, for example, the amino alcohol may be present in an amount of greater than 0 to 0.5 wt %, or an amount of 0.5 wt % or more (e.g., an amount of 0.5 wt % to the solubility limit of the amino alcohol in the water or organic solvent), based on the total weight of the solution. In some embodiments, the amino alcohol is present in the solution in an amount of 0.4 to 40 vol %, based on the total volume of the solution. For example, the amino alcohol may be present in the solution in an amount of 0.4 vol %, based on the total volume of the solution. At higher concentrations of the amino alcohol (e.g., concentrations above 1.5 wt %, based on the total weight of the solution), treatment layers formed from amino alcohols that are solids at room temperature may exhibit poor adhesion performance, while treatment layers formed from amino alcohols that are liquids at room temperature may exhibit improved adhesion, but may also exhibit water sensitivity if there is an excessive amount of unreacted hydroxyl groups.

According to certain embodiments, when the amino alcohol is present in the solution in an amount of 0.5 wt % or more, based on the total weight of the solution, the method can further include rinsing the solution (or the treatment layer formed from the solution) after the solution is applied on at least a portion of the sol-gel conversion coating. For example, the solution can be applied on at least a portion of the sol-gel conversion coating, and the solution can remain on the sol-gel conversion coating for a time period of 10 minutes to less than 16 hours, for example, a time period of 30 minutes. Then, the solution (e.g., the article or treatment layer) on the sol-gel conversion coating can be rinsed with water or the organic solvent. Alternatively, when the amino alcohol is present in the solution in an amount of 0.5 wt % or less, based on the total weight of the solution, the rinsing may be omitted.

In the embodiment shown in FIG. 3, the method (200) further includes at least partially drying the solution including the amino alcohol to form the treatment layer (208). In certain embodiments, the at least partially drying can be performed for a time period of 10 minutes to less than 16 hours. The at least partially drying can be performed at a temperature of 14° C. to 31° C. Alternatively, the at least partially drying can be performed at an elevated temperature for a shorter period of time, for example at 50° C. for 10 minutes to not more than 4 hours. When the amino alcohol is present in the solution in an amount of 0.5 wt % or less, based on the total weight of the solution, the above-described rinsing of the solution (or the treatment layer) may be omitted and the solution may be directly dried to form the treatment layer on the sol-gel conversion coating.

Figure 4:
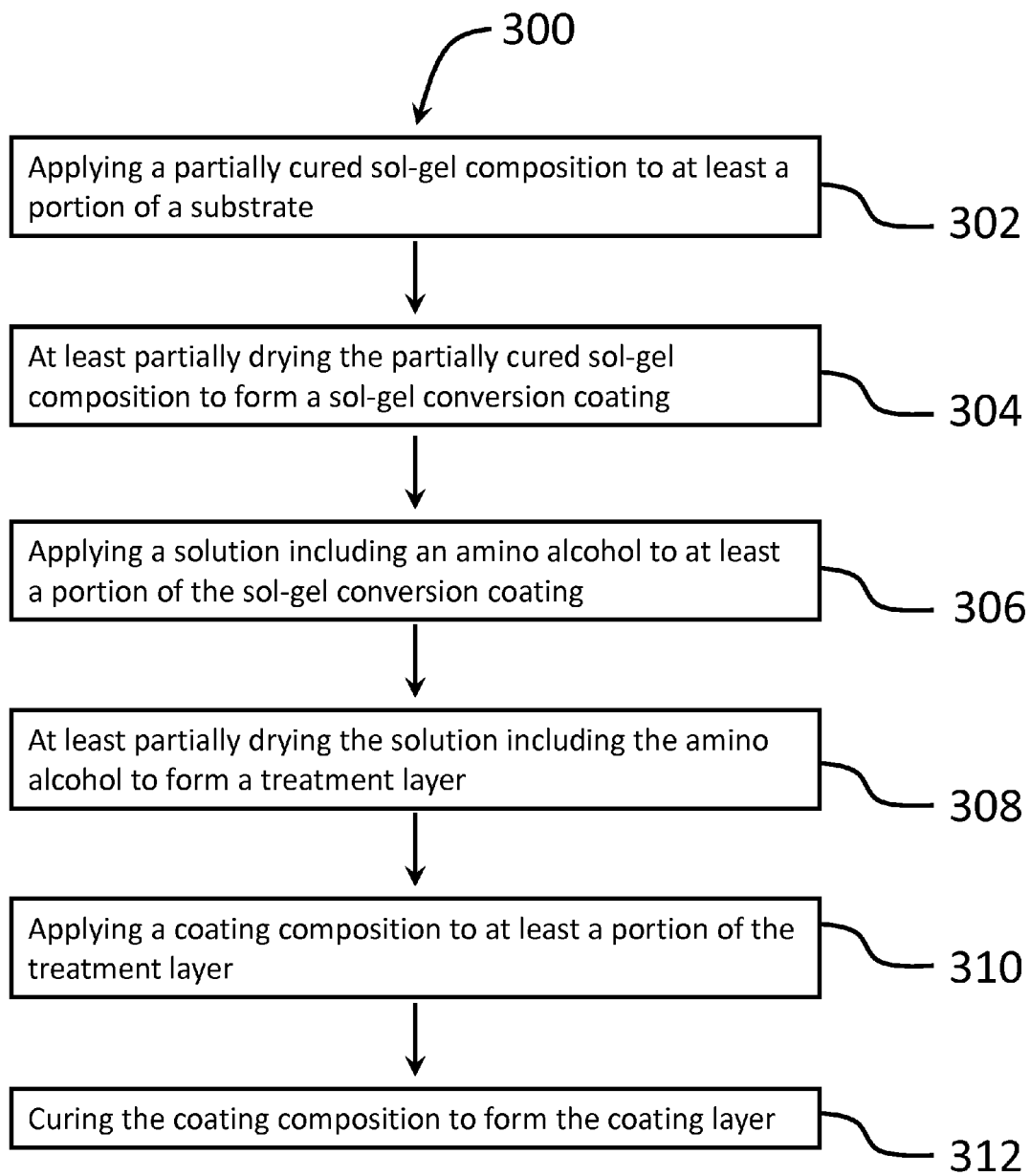
FIG. 4 is a flowchart illustrating a method of manufacturing an article according to another embodiment of the present disclosure.

A method of manufacturing an article according to another embodiment of the present disclosure is illustrated by the flowchart of FIG. 4. According to that embodiment, a method (300) includes applying a partially cured sol-gel composition to at least a portion of a substrate (302), at least partially drying the partially cured sol-gel composition to form a sol-gel conversion coating (304) (e.g., a partially or fully cured sol-gel conversion coating), applying a solution including an amino alcohol to at least a portion of the sol-gel conversion coating (306), at least partially drying the solution including the amino alcohol to form a treatment layer (308), and may include further curing the partially cured sol-gel composition (or at least partially curing an uncured sol-gel composition) as described above with respect to FIG. 3. The method (300) is not limited to applying a partially cured sol-gel composition, but may instead include applying an uncured sol-gel composition to at least a portion of the substrate. The method (300) further includes applying a coating composition to at least a portion of the treatment layer (310). The coating composition can be any suitable coating composition, such as those described above, or any suitable coating composition used in the art. The method (300) further includes curing the coating composition to form the coating layer (312). Those of skill in the art would readily appreciate the conditions for curing the coating composition and, therefore, those conditions will not be further described here.

Embodiments of the present disclosure are further described below with reference to the following examples. The examples, however, are not intended to limit the scope of the present disclosure. For example, while the examples include an amino alcohol including tris(hydroxymethyl)aminomethane, it will be understood that other amino alcohols or mixtures of amino alcohols, such as amino methyl propanediol, amino ethyl propanediol, amino methyl propanol, dimethyl amino ethanol, amino hydroxyethyl pentanediol, amino pentanediol, and/or amino methyl butanol, can be substituted for or mixed with the tris(hydroxymethyl)aminomethane.

Example 1

A substrate including 2024 T3 aluminum alloy clad with aluminum was prepared for sol-gel pretreatment by abrasive scrubbing of the substrate using deionized water and a Scotch-brite #7447 abrasive pad (available from the 3M Company) until a water break-free surface was obtained. As used herein, the term "water break-free surface" refers to a surface capable of having an unbroken sheet of water on the surface that does not bead up or drain off when the surface is held in a vertical position. The substrate was rinsed with deionized water and wiped with a paper towel to remove smut (e.g., residues). The substrate was rinsed again to remove lint and/or particulates left behind by the paper towel and dried in air at ambient temperature.

A sol-gel composition (Desogel EAP-9, available from, PPG Aerospace) was applied to the substrate using a high-volume low-pressure (HVLP) spray application gun. The sol-gel composition was dried for a time period of 10 minutes in air at ambient temperature. After 10 minutes of air drying, excess material was removed from the substrate by blotting or wiping the excess material with an absorbent paper towel, lint free cotton cloth or nylon pad. The sol-gel composition was partially cured overnight in air at ambient temperature for a time period of 20 hours to form a partially cured sol-gel conversion coating.

A treatment layer including an amino alcohol was formed on the substrate by applying an aqueous solution including tris(hydroxymethyl)aminomethane in an amount of 40 wt % (based on the total weight of the aqueous solution) to the sol-gel conversion coating using an HVLP spray application gun over a time period of 5 minutes. The tris(hydroxymethyl)aminomethane was dried on the substrate in air at ambient temperature for a time period of 30 minutes. Excess tris(hydroxymethyl)aminomethane was rinsed off of the substrate using a deionized water spray rinse for 1 minute. The substrate was then dried in air at ambient temperature for 15 to 30 minutes.

Then, a coating layer was formed on the treatment layer using a polyurethane-based coating composition including 80-90 wt % (here, 84 wt %) DEFTHANE® ELT (DEFTHANE® is a registered trademark of PRC-DeSoto International, Inc., Sylmar, Calif.) and 10-20 wt % (here, 16 wt %) wt % wollastonite, based on the total weight of the polyurethane-based coating composition. The polyurethane-based coating composition was applied to the treatment layer using an HVLP spray application gun. The coating layer was formed to a dry film thickness of 2.5-3.5 mils, and was then fully cured for 14 days in air at ambient temperature to form a coated substrate.

Example 2

A coated substrate was formed as in Example 1, except that 12 wt % of Hybricor 294 (available from Wayne Pigment Corp., Milwaukee, Wis.) was used instead of the wollastonite.

Example 3

A coated substrate was formed as in Example 1, except that the amount of tris(hydroxymethyl)aminomethane in the aqueous solution was 2 wt % instead of 40 wt %, and excess tris(hydroxymethyl)aminomethane was not rinsed off of the substrate.

Example 4

A coated substrate was formed as in Example 3, except that the amount of tris(hydroxymethyl)aminomethane in the aqueous solution was 1.5 wt % instead of 2 wt %.

Example 5

A coated substrate was formed as in Example 3, except that the amount of tris(hydroxymethyl)aminomethane in the aqueous solution was 1 wt % instead of 2 wt %.

Example 6

A coated substrate was formed as in Example 3, except that the amount of tris(hydroxymethyl)aminomethane in the aqueous solution was 0.5 wt % instead of 2 wt %.

Example 7

A coated substrate was formed as in Example 1, except that AC-131 (available from 3M Corporation) was used instead of Desogel EAP-9, the amount of tris(hydroxymethyl)aminomethane in the aqueous solution was 0.5 vol %, based on the total volume of the aqueous solution, instead of 40 wt %, and excess tris(hydroxymethyl)aminomethane was not rinsed off of the substrate.

Example 8

A coated substrate was formed as in Example 7, except that the amount of tris(hydroxymethyl)aminomethane in the aqueous solution was 1.5 vol %, instead of 0.5 vol %.

Example 9

A coated substrate was formed as in Example 1, except that AC-131 (available from 3M Corporation) was used instead of Desogel EAP-9, the aqueous solution included 0.5 vol % amino ethyl propanediol, based on the total volume of the aqueous solution, instead of 40 wt % of tris(hydroxymethyl)aminomethane, and excess amino ethyl propanediol was not rinsed off of the substrate.

Example 10

A coated substrate was formed as in Example 9, except that the aqueous solution included 1.5 vol % amino ethyl propanediol, instead of 0.5 vol %.

Example 11

A coated substrate was formed as in Example 1, except that AC-131 (available from 3M Corporation) was used instead of Desogel EAP-9, the aqueous solution included 0.5 vol % amino methyl propanediol, based on the total volume of the aqueous solution, instead of 40 wt % tris(hydroxymethyl)aminomethane, and excess amino methyl propanediol was not rinsed off of the substrate.

Example 12

A coated substrate was formed as in Example 11, except that the aqueous solution included 1.5 vol % amino methyl propanediol, instead of 0.5 vol %.

Example 13

A coated substrate was formed as in Example 1, except that AC-131 (available from 3M Corporation) was used instead of Desogel EAP-9, the aqueous solution included 0.5 vol % amino methyl propanol, based on the total volume of the aqueous solution, instead of 40 wt % tris(hydroxymethyl)aminomethane, and excess amino methyl propanol was not rinsed off of the substrate.

Example 14

A coated substrate was formed as in Example 13, except that the aqueous solution included 1.5 vol % amino methyl propanol, instead of 0.5 vol %.

Example 15

A coated substrate was formed as in Example 1, except that AC-131 (available from 3M corporation) was used instead of Desogel EAP-9, the aqueous solution included 0.5 vol % dimethyl amino ethanol, based on the total volume of the aqueous solution, instead of 40 wt % tris(hydroxymethyl)aminomethane, and excess dimethyl amino ethanol was not rinsed off of the substrate.

Example 16

A coated substrate was formed as in Example 15, except that the aqueous solution included 1.5 vol % dimethyl amino ethanol, instead of 0.5 vol %.

Example 17

A coated substrate was formed as in Example 1, except that AC-131 (available from 3M Corporation) was used instead of Desogel EAP-9, the aqueous solution included 0.5 vol % amino methyl butanol, based on the total volume of the aqueous solution, instead of 40 wt % tris(hydroxymethyl)aminomethane, and excess amino methyl butanol was not rinsed off of the substrate.

Example 18

A coated substrate was formed as in Example 17, except that the aqueous solution included 1.5 vol % dimethyl amino ethanol, instead of 0.5 vol %.

Example 19

A coated substrate was formed as in Example 1, except that AC-131 (available from 3M Corporation) was used instead of Desogel EAP-9, the aqueous solution included 0.5 vol % amino pentanediol, based on the total volume of the aqueous solution, instead of 40 wt % tris(hydroxymethyl) aminomethane, and excess amino pentanediol was not rinsed off of the substrate.

Example 20

A coated substrate was formed as in Example 19, except that the aqueous solution included 1.5 vol % amino pentanediol, instead of 0.5 vol %.

Example 21

A coated substrate was formed as in Example 1, except that AC-131 (available from 3M Corporation) was used instead of Desogel EAP-9, the aqueous solution included 0.5 vol % amino hydroxyethyl pentanediol, based on the total volume of the aqueous solution, instead of 40 wt % tris (hydroxymethyl)aminomethane, and excess amino hydroxy ethyl pentanediol was not rinsed off of the substrate.

Example 22

A coated substrate was formed as in Example 21, except that the aqueous solution included 1.5 vol % amino hydroxyethyl pentanediol, instead of 0.5 vol %.

Example 23

A coated substrate was formed as in Example 1, except that AC-131 (available from 3M Corporation) was used instead of Desogel EAP-9, 100 wt % of DEFTHANE AMC® (available from PRC-DeSoto International, Inc., Sylmar, Calif.)(DEFTHANE® is a registered trademark of PRC-DeSoto International, Inc., Sylmar, Calif.), based on the total weight of the polyurethane-based coating composition, was used instead of DEFTHANE® ELT (DEFTHANE® is a registered trademark of PRC-DeSoto International, Inc., Sylmar, Calif.) and wollastonite, and excess tris(hydroxymethyl)aminomethane was not rinsed off of the substrate.

Comparative Example 1

A coated substrate was formed as in Example 2, except that the coated substrate did not include the treatment layer.

Comparative Example 2

A coated substrate was formed as in Example 1, except that the coated substrate did not include the treatment layer.

Comparative Example 3

A coated substrate was formed as in Example 23, except that the treatment layer was not formed.

Average Dry Adhesion

The coated substrates according to Examples 1 and 2, and Comparative Examples 1 and 2, and coated substrates according to Examples 3-26 and Comparative Examples 3-6 were tested for adhesion to the substrate by cutting a 45 degree crosshatch scribe pattern through the cured coating to the base metal, applying Tape No. 250 (available from 3M Company), removing the tape in one continuous motion, and examining the tested area for coating removal. The coated substrates were visually inspected and rated according to a scale of 0 to 10, where 0 corresponds to poor dry adhesion and 10 corresponds to good dry adhesion. The results of the tests for each set of three coated substrates according to Examples 1 and 2, and Comparative Examples 1 and 2 are shown in Table 1 below. The results for the coated substrates according to Examples 3-10 and Comparative Examples 3 and 4 are shown in Table 2 below. The results for the coated substrates according to Examples 11-26 are shown in Table 3 below. The results for the coated substrates according Examples 27 and 28, and Comparative Examples 5 and 6 are shown in Table 4 below.

Average Wet Adhesion

Three sets of coated substrates according to Examples 1 and 2, and Comparative Examples 1 and 2, and coated substrates according to Examples 3-26 and Comparative Examples 3-6 were tested for adhesion to the substrate by first curing and immersing the substrates in deionized water for 7 days, then cutting a 45 degree crosshatch scribe pattern into the coating to the base metal, applying Tape No. 250 (available from 3M Company), removing the tape in one continuous motion, and examining the tested area for coating removal. The coated substrates were visually inspected and rated according to a scale of 0 to 10, where 0 corresponds to poor wet adhesion and 10 corresponds to good wet adhesion. The results of the tests for each set of three coated substrates according to Examples 1 and 2, and Comparative Examples 1 and 2 are shown in Table 1 below. The results for the coated substrates according to Examples 3-10 and Comparative Examples 3 and 4 are shown in Table 2 below. The results for the coated substrates according to Examples 11-26 are shown in Table 3 below. The results for the coated substrates according Examples 27 and 28, and Comparative Examples 5 and 6 are shown in Table 4 below.

Salt Spray Test

Three sets of coated substrates according to Examples 1 and 2, and Comparative Examples 1 and 2 were tested using a neutral salt spray for 3,000 hours according to ASTM B-117 test specification. The results of the tests for each set of three coated substrates according to Examples 1 and 2, and Comparative Examples 1 and 2 are shown in Table 1 below.

Filiform Corrosion Test

Three sets of coated substrates according to Examples 1 and 2, and Comparative Examples 1 and 2, and coated substrates according to Examples 3-23 and Comparative Example 3 were prepared and tested by scribing two 1 mm wide diagonal lines across the panel, exposing the scribed panels to concentrated HCl fumes for one hour, and then placing the exposed panels into an environmental chamber capable of maintaining the relative humidity at 80 percent and a temperature of 35° C. for 720 hours.

Uniform etch corrosion (UEC) measurements (as a measure of filiform corrosion) were also taken for the coated substrates according to Examples 3-23 and Comparative Example 3. UEC results from a direct chemical attack on a metal surface (i.e., HCl exposure) and involves only the metal surface. On a polished surface, this type of corrosion is first seen as a general dulling of the surface, and if the attack is allowed to continue, the surface becomes rough and possibly frosted in appearance. The UEC measurements were graded in accordance with the ASTM D1654-05 grading system.

The adhesion and corrosion test results for each set of three coated substrates according to Examples 1 and 2, and Comparative Examples 1 and 2 are shown in Table 1 below. The results for the coated substrates according to Examples 3-6 are shown in Table 2 below. The results for the coated substrates according to Examples 7-22 are shown in Table 3 below. The results for the coated substrates according Example 23, and Comparative Example 3 are shown in Table 4 below.

TABLE 1

|  | Avg. Dry Adhesion | Avg. Wet Adhesion | Salt Spray ** | | | Filiform Corrosion | | |
| --- | --- | --- | --- | --- | --- | --- | --- | --- |
| Example 1 | 10 | 9 | No corrosion, no blisters | No corrosion, no blisters | No corrosion, no blisters | Pass | Pass | Pass |
| Example 2 | 10 | 9 | One blister | One blister | One blister | Fail | Fail | Fail |
| Comparative Example 1 | 9.67 | 5.33 | Fail, blisters | Fail, blisters | Fail, blisters | Fail | Fail | Fail |
| Comparative Example 2 | 10 | 6 | Fail, blisters | Fail, blisters | Fail, blisters | Fail | Fail | Fail |

As can be seen from the results shown in Table 1, the coated substrates prepared as in Examples 1 and 2 exhibited improved wet adhesion after immersion in deionized water for 7 days, and exhibited improved neutral salt spray corrosion test results, particularly, Example 1.

TABLE 2

|  | Dry Adhesion | Wet Adhesion | Filiform Ratings | | | NSS Rating | |
| --- | --- | --- | --- | --- | --- | --- | --- |
|  |  |  | Filiform | UEC | Field | Scribe | Field |
| Example 3 | 9.5 | 0 | 9.0 | 1.0 | 10.0 | 6.0 | 8.0 |
| Example 4 | 9.2 | 7 | 10.0 | 3.0 | 10.0 | 5.0 | 8.0 |
| Example 5 | 9.5 | 9 | 10.0 | 4.0 | 10.0 | 6.0 | 8.0 |
| Example 6 | 9.7 | 9.5 | 10.0 | 6.0 | 10.0 | 9.0 | 10.0 |

TABLE 3

|  | Dry Adhesion | Wet Adhesion | Wet Adhesion Blistering | Filiform Corrosion | UEC |
| --- | --- | --- | --- | --- | --- |
| Example 7 | 9.75 | 9.75 | 0 | 8.5 | 6 |
| Example 8 | 9.75 | 0 | 40 | 7.5 | 4.5 |
| Example 9 | 9.25 | 9.75 | 0 | 10 | 6 |
| Example 10 | 9.75 | 9.5 | 0 | 7.5 | 5.5 |
| Example 11 | 9.75 | 9.25 | 0 | 7 | 5 |
| Example 12 | 9.75 | 9 | 5-10% | 6 | 4.5 |
| Example 13 | 9.75 | 9.75 | 0 | 8.5 | 6.5 |
| Example 14 | 9.75 | 9.75 | 0 | 7.5 | 6 |
| Example 15 | 9.75 | 9.0 | 0 | 7.5 | 5.5 |
| Example 16 | 9.75 | 5 | 10 | 7.5 | 5.5 |
| Example 17 | 9.75 | 9.75 | 0 | 9 | 6.5 |
| Example 18 | 9.75 | 9.75 | 0 | 8.5 | 6 |
| Example 19 | 9.75 | 8.5 | 5 | 7 | 5 |
| Example 20 | 9.75 | 2 | 5 | 6 | 4 |
| Example 21 | 9.75 | 9 | 0 | 9.5 | 7 |
| Example 22 | 9.75 | 9.75 | 0 | 8 | 7 |

TABLE 4

|  | Dry Adhesion | Wet Adhesion | Wet Adhesion Blistering (%) | Filiform Corrosion UEC/Scribe/Field |
| --- | --- | --- | --- | --- |
| Comparative Example 3 | 9 | 8 | 0 | 5/5/8 |
| Example 23 | 9.5 | 9.5 | 0 | 4/7/9 |

Whereas particular embodiments of the present disclosure have been described above for purposes of illustration, it will be understood by those skilled in the art that numerous variations of the details of the present disclosure may be made without departing from the invention as defined in the appended claims, and equivalents thereof. For example, although embodiments herein have been described in connection with "a" treatment layer, "a" coating layer, and the like, one or more of these components or any of the other components recited can be used according to the present disclosure.

Although various embodiments of the present disclosure have been described in terms of "comprising" or "including," embodiments consisting essentially of or consisting of are also within the scope of the present disclosure. For example, while the present disclosure describes a treatment layer including an amino alcohol and a solution including an amino alcohol, a treatment layer and/or a solution consisting essentially of or consisting of an amino alcohol is also within the scope of the present disclosure. Thus, as described above, the treatment layer may be formed from a solution consisting essentially of the amino alcohol. In this context, "consisting essentially of" means that any additional components in the solution or treatment layer will not materially affect the adhesion of the treatment layer to another layer, such as the sol-gel conversion layer and/or coating layer.

Additionally, although embodiments herein have been described in connection with coating layers including polyurethane and/or formed from a coating composition including a hydroxyl functional polyol and a polyisocyanate, other coating layers including a functional group capable of reacting with a hydroxyl group of the amino alcohol can be used.

As used herein, unless otherwise expressly specified, all numbers such as those expressing values, ranges, amounts or percentages may be read as if prefaced by the word "about," even if the term does not expressly appear. Further, use of the word "about" reflects the penumbra of variation associated with measurement, significant figures, and interchangeability, all as understood by a person having ordinary skill in the art to which this disclosure pertains. Any numerical range recited herein is intended to include all sub-ranges subsumed therein. Plural encompasses singular and vice versa. For example, while the present disclosure describes "an" amino alcohol, a mixture of such amino alcohols can be used. Also, as used herein, the term "polymer" is meant to refer to prepolymers, oligomers, and both homopolymers and copolymers; the prefix "poly" refers to two or more. When ranges are given, any endpoints of those ranges and/or numbers within those ranges can be combined within the scope of the present disclosure. The terms "including" and like terms mean "including but not limited to." Similarly, as used herein, the terms "on," "applied on," and "formed on" mean on, applied on, or formed on, but not necessarily in contact with the surface. For example, a coating layer "formed on" a substrate does not preclude the presence of one or more other coating layers of the same or different composition located between the formed coating layer and the substrate.

Notwithstanding that the numerical ranges and parameters set forth herein may be approximations, numerical values set forth in the specific examples are reported as precisely as is practical. Any numerical value, however, inherently contains certain errors necessarily resulting from the standard variation found in their respective testing measurements. The word "comprising" and variations thereof as used in this description and in the claims do not limit the disclosure to exclude any variants or additions.

What is claimed is:

1. An article, comprising:
    a substrate;
    a sol-gel conversion coating on at least a portion of the substrate, the sol-gel conversion coating comprising a functional group; and
    a treatment layer on at least a portion of the sol-gel conversion coating, the treatment layer formed from a solution comprising an amino alcohol present in the solution in an amount of 0.4 vol % to 40 vol %, based on total volume of the solution, wherein an amine group of the amino alcohol reacts with the functional group of the sol-gel conversion coating to form an amine linkage.

2. The article of claim 1, further comprising a coating layer on at least a portion of the treatment layer, the coating layer comprising a second functional group, wherein a hydroxyl group of the amino alcohol of the treatment layer reacts with the second functional group of the coating layer.

3. The article of claim 2, wherein the coating layer comprises a polyurethane-based coating composition.

4. The article of claim 1, wherein the amino alcohol comprises a compound represented by $[N(R_1)(R_2)]_z$—R—$(R'$—$OH)_x R''_y$, wherein:
    x is 1 to 3;
    y is 0 to 2;
    z is 1 to 3;
    x+y+z=4;
    $R_1$ and $R_2$ each independently comprise a hydrogen atom or a C1 to C6 alkyl group, and when z is greater than 1, each $R_1$ and each $R_2$ may be the same or different;
    R and R' each independently comprise a C1 to C30 alkylene group, and when x is greater than 1, each R' may be the same or different; and
    R" comprises a hydrogen atom or a C1 to C30 alkyl group, and when y is greater than 1, each R" may be the same or different.

5. The article of claim 4, wherein x equals 1.

6. The article of claim 1, wherein the amino alcohol comprises tris(hydroxymethyl)aminomethane, amino methyl propanediol, amino ethyl propanediol, amino methyl propanol, dimethyl amino ethanol, amino hydroxyethyl pentanediol, amino pentanediol, and/or amino methyl butanol.

7. The article of claim 1, wherein the amino alcohol comprises tris(hydroxymethyl)aminomethane.

8. An article, comprising:
    a substrate;
    a sol-gel conversion coating on at least a portion of the substrate, the sol-gel conversion coating comprising a functional group;
    a treatment layer on at least a portion of the sol-gel conversion coating, the treatment layer formed from a solution comprising an amino alcohol present in the solution in an amount of 0.4 vol % to 40 vol %, based on total volume of the solution, wherein an amine group of the amino alcohol reacts with the functional group of the sol-gel conversion coating to form an amine linkage; and
    a coating layer on at least a portion of the treatment layer, the coating layer comprising a polyurethane-based coating composition comprising an isocyanate group, wherein the isocyanate group reacts with a hydroxyl group of the amino alcohol to form a urethane linkage.

9. The article of claim 8, wherein the amino alcohol comprises a compound represented by $[N(R_1)(R_2)]_z$—R—$(R'$—$OH)_x R''_y$, wherein:
    x is 1 to 3;
    y is 0 to 2;
    z is 1 to 3;
    x+y+z=4;
    $R_1$ and $R_2$ each independently comprise a hydrogen atom or a C1 to C6 alkyl group, and when z is greater than 1, each $R_1$ and each $R_2$ may be the same or different;
    R and R' each independently comprise a C1 to C30 alkylene group, and when x is greater than 1, each R' may be the same or different; and
    R" comprises a hydrogen atom or a C1 to C30 alkyl group, and when y is greater than 1, each R" may be the same or different.

10. The article of claim 8, wherein the amino alcohol comprises tris(hydroxymethyl)aminomethane.

11. The article of claim 1, wherein the article comprises an aerospace vehicle part.

12. The article of claim 8, wherein the article comprises an aerospace vehicle part.

* * * * *